United States Patent [19]
Yanni et al.

[11] Patent Number: 5,475,034
[45] Date of Patent: Dec. 12, 1995

[54] TOPICALLY ADMINISTRABLE COMPOSITIONS CONTAINING 3-BENZOYLPHENYLACETIC ACID DERIVATIVES FOR TREATMENT OF OPHTHALMIC INFLAMMATORY DISORDERS

[75] Inventors: John M. Yanni, Burleson; Gustav Graff, Cleburne; Mark R. Hellberg, Arlington, all of Tex.

[73] Assignee: Alcon Laboratories, Inc., Fort Worth, Tex.

[21] Appl. No.: 254,090

[22] Filed: Jun. 6, 1994

[51] Int. Cl.$^6$ .................................. A61K 31/165
[52] U.S. Cl. ...................... 514/619; 514/535; 514/570; 514/617; 514/618; 514/621
[58] Field of Search ................... 564/169; 514/621, 514/619, 617, 618

[56] References Cited

U.S. PATENT DOCUMENTS

| | | | |
|---|---|---|---|
| 3,828,093 | 8/1974 | Bays et al. | 260/469 |
| 4,045,576 | 8/1977 | Welstead, Jr. et al. | 424/309 |
| 4,126,635 | 11/1978 | Welstead, Jr. et al. | 562/441 |
| 4,182,774 | 1/1980 | Welstead, Jr. et al. | 424/309 |
| 4,254,146 | 3/1981 | Walsh | 424/309 |
| 4,318,949 | 2/1982 | Shanklin, Jr. et al. | 424/248.56 |
| 4,503,073 | 3/1985 | Walsh et al. | 514/539 |
| 4,568,695 | 2/1986 | Moran et al. | 514/648 |
| 4,683,242 | 7/1987 | Poser | 514/539 |
| 4,783,487 | 11/1988 | Brune | 514/563 |
| 4,851,443 | 7/1989 | Brune | 514/563 |
| 4,910,225 | 3/1990 | Ogawa et al. | 514/561 |

FOREIGN PATENT DOCUMENTS

| | | |
|---|---|---|
| 2071086 | 9/1981 | United Kingdom . |
| 2093027 | 8/1982 | United Kingdom . |

OTHER PUBLICATIONS

Sancillo et al., "AHR–10037, a non–steroidal anti–inflammatory compound of low gastric toxicity," *Agents and Actions*, 31:117–126 (1990).

Walsh et al., "Antiinflammatory Agents. 3. Synthesis and Pharmacological Evaluation of 2–Amino–3–benzoylphenylacetic Acid and Analogues," *J. Med. Chem.* 27:1379–1388 (1984).

Walsh et al., "Antiinflammatory Agents. 4. Synthesis and Biological Evaluation of Potential Prodrugs of 2–Amino–3–benzoylbenzeneacetic Acid and 2–Amino–3–(4–chlorobenzoyl)benzeneacetic Acid," *J. Med. Chem.* 33:2296–2304 (1990).

*Primary Examiner*—Shailendra Kumar
*Attorney, Agent, or Firm*—Patrick M. Ryan

[57] ABSTRACT

Novel ester and amide derivatives of 3-benzoylphenylacetic acid are disclosed. The use of these novel derivatives and certain known derivatives in topically administrable compositions for the treatment of ophthalmic inflammatory disorders is also disclosed.

7 Claims, No Drawings

TOPICALLY ADMINISTRABLE COMPOSITIONS CONTAINING 3-BENZOYLPHENYLACETIC ACID DERIVATIVES FOR TREATMENT OF OPHTHALMIC INFLAMMATORY DISORDERS

FIELD OF THE INVENTION

This invention relates to topically administrable compositions for the treatment of inflammatory disorders. In particular, this invention relates to non-irritating, topically administrable compositions containing 3-benzoylphenylacetic acid derivatives for the treatment of ophthalmic inflammatory disorders.

BACKGROUND OF THE INVENTION 3-benzoylphenylacetic acid and certain of its derivatives are known to possess anti-inflammatory activity. U.S. Pat. Nos. 4,254,146, 4,045,576, 4,126,635, and 4,503,073, and U.K. Patent Application Nos. 2,071,086A and 2,093,027A teach various 3-benzoylphenylacetic acids, salts and esters, and hydrates thereof, having anti-inflammatory activity. U.S. Pat. No. 4,568,695 teaches 2-amino-3-benzoylphenylethyl alcohols having anti-inflammatory activity. U.S. Pat. No. 4,313,949 teaches 2-amino-3-benzoyl-phenylacetamides having anti-inflammatory activity.

Each of the above-listed patents or patent applications, all of which are assigned in whole or in part to A. H. Robins, contains an identical disclosure regarding formulations of the 3-benzoylphenylacetic acid or acid derivative. Each of the above also contains the same disclosure regarding administration routes for the drug formulation. The only formulation examples in the A. H. Robins patents or patent applications are capsules, tablets and "injectable-2% sterile solutions," and the only administration routes mentioned are oral (as in capsules or tablets) parenteral (in the form of sterile solutions or suspensions), and, in some cases intravenous (in the form of sterile solutions). No topical or local administration is taught by any of the above-listed patents or patent applications.

Certain derivatives of 2-amino-3-benzoylbenzeneacetic acid (amfenac) and 2-amino-3-(4-chloro-benzoyl)benzeneacetic acid have also been evaluated by Walsh et al., J. Med. Chem., 33:2296–2304 (1990), in an attempt to discover nonsteroidal anti-inflammatory prodrugs with minimal or no gastrointestinal side effects upon oral administration.

In contrast, U.S. Pat. No. 4,683,242 teaches the transdermal administration of 2-amino-3-benzoylphenylacetic acids, salts, and esters, and hydrates and alcoholates thereof to control inflammation and alleviate pain.

U.S. Pat. No. 4,910,225 teaches certain benzoylphenylacetic acids for local administration to control ophthalmic, nasal or otic inflammation. Only acetic acids are disclosed in the '225 patent; no esters or amides are mentioned or taught as anti-inflammatory agents for local administration to the eyes, nose and ears.

Although benzoylphenylacetic acids are effective in suppressing ocular inflammation, their full anti-inflammatory potential has not yet been approached due to their generally slow rate of penetration through the cornea. Relatively high concentrations of these drugs are often needed to achieve corneal penetration rates sufficient to provide effective intraocular drug concentrations. Such high drug concentrations are generally not desirable as they may provoke ocular irritation and discomfort.

Additionally, the acetic acid compounds taught in the '225 patent are difficult to formulate in stable aqueous solutions. The '225 patent solves this problem by incorporating a water-soluble polymer and sulfite, and adjusting the pH to about 6.0 to 9.0, preferably about 7.5–8.5. Water soluble polymers taught by the '225 patent include polyvinyl pyrrolidone, carboxypropylcellulose, hydroxyethylcellulose, hydroxypropylcellulose, polyvinyl alcohol, sodium salt of polyacrylic acid and so on. Polyvinyl pyrrolidone is preferred. The concentration of water soluble polymer is in the range of 0.1 to 10 w/w %. Sulfite includes sodium, potassium, magnesium, and calcium sulfite salt and so on. The concentration is in the range of about 0.1 to 1.0 w/w %.

What is needed are additional non-steroidal, topically administrable anti-inflammatory agents which are stable, non-irritating at therapeutic doses, and at least as potent as benzoylphenylacetic acids in suppressing ocular inflammation.

SUMMARY OF THE INVENTION

It has now been found that certain novel and certain known 3-benzoylphenylacetic acid derivatives are useful as topically administrable anti-inflammatory compounds for treating ophthalmic inflammatory disorders. Converting the free acetic acid functional group to an ester or an amide enhances compound stability by slowing the rate of lactam formation. Among other factors, the present invention is based on the finding that certain 3-benzoylphenylacetic acid derivatives which show no significant anti-inflammatory activity in vitro are, in fact, as active or even more active than the parent 3-benzoylphenylacetic acids when administered topically to the eye.

Accordingly, the present invention is directed to novel derivatives of 3-benzoylphenylacetic acid compounds. The present invention is also directed to pharmaceutical compositions suitable for topical ophthalmic administration which contain an anti-inflammatory-effective amount of a 3-benzoylphenylacetic acid derivative, and to a method of treating ophthalmic inflammatory disorders which comprises topically administering to the eye a 3-benzoylphenylacetic acid derivative.

DETAILED DESCRIPTION OF THE INVENTION

As used herein, "(un)branched" means optionally branched, and "(un)substituted" means optionally substituted.

The novel 3-benzoylphenylacetic acid derivative compounds of the present invention have the following structural formula:

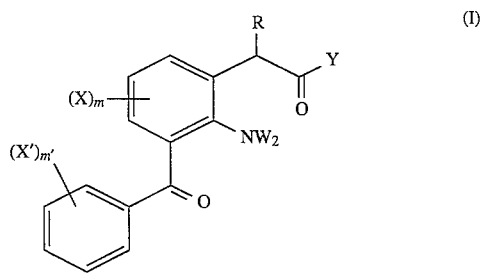

W=O,H
R=H, $C_{1-4}$(un)branched alkyl, $CF_3$, $SR^4$ $Y=OR^5, NR^5R^6$
$R^5=-(CH_2)_r-Z^2-(CH_2)_r\cdot A, -(CH_2)_r-Z^3-(CH_2)_r\cdot A'$
$r=2-6$
$r'=0-6$
$Z^2=O, C=O, OC(=O), C(=O)NR^3, NR^3C(=O), -S(O)_{n2}CH_2-, S, CHOR^3, NR^3$
$Z^3=$nothing, $-CHR^4-, -CR^4R^4-$
$r^2=1,2$
$R^3=$H, $C_{1-6}$(un)branched alkyl, (un)substituted aryl (substitution as defined by X below), (un)substituted heterocycle (substitution as defined by X below)
A=H, OH, (un)substituted aryl (substitution as defined by X below), (un)substituted heterocycle, $-(CH_2)_rOR^3$
A'=OH, (un)substituted aryl (substitution as defined by X below), (un)substituted heterocycle (substitution as defined by X below), $-(CH_2)_rOR^3$
$R^4=C_{1-6}$(un)branched alkyl
$R^6=$H, $OR^7$
$R^7=$H, $C_{1-6}$(un)branched alkyl, (un)substituted aryl (substitution as defined by X below)
X and X' independently=H, F, Cl, Br, I, $OR^7$, CN, OH, $S(O)_{n2}R^4$, $CF_3$, $R^4$, $NO_2$
$m=0-3$
$m'=0-5$
$n^2=0-2$ The preferred, novel 3-benzoylphenylacetic acid derivatives are those wherein:
W=H
R=H, $CH_3$
$Y=NR^5R^6$, $-$NHOH
$R^4=C_{1-4}$(un)branched alkyl
$R^5=-(CH_2)_r-Z^2-(CH_2)_r\cdot -A, -(CH_2)_r-Z^3-(CH_2)_r\cdot -A'$
$r=2-4$
$r'=0-2$
$Z^2=O$
$Z^3=$nothing
A=H
A'=(un)substituted aryl (substitution as defined by X below)
$R^6=$H, $OR^7$
$R^7=$H, $C_{1-2}$ alkyl
X and X' independently=H, F, Cl, Br, $CF_3$, $S(O)_{n2}R^4$, $OR^7$
$m=0-2$
$m'=0-3$
$n^2=0$ The 3-benzoylphenylacetic acid derivative compounds useful in the topically administrable ophthalmic compositions of the present invention are represented by the following structural formula which includes both known derivatives and the novel derivatives of the present invention:

[Structure I shown: a substituted benzophenone with (X)_m, (X')_m', R, Y, O, NW_2 substituents]

R=H, $C_{1-4}$ (un)branched alkyl, $CF_3$, $SR^4$
Y=OR', NR"R'
R'=H (except when Y=OR'), $C_{1-10}$ (un)branched alkyl, (un)substituted (substitution as defined by X below), (un)substituted heterocycle (substitution as defined by X below), $-(CH_2)_nZ(CH_2)_n\cdot A$
$n=2-6$
$n'=1-6$
Z=nothing, O, C=O, OC(=O), C(=O)O, C(=O)NR^3, $NR^3C(=O)$, $S(O)_{n2}$, $CHOR^3$, $NR^3$
$n^2=0-2$
$R^3=$H, $C_{1-6}$ (un)branched alkyl, (un)substituted aryl (substitution as defined by X below), (un)substituted heterocycle (substitution as defined by X below)
A=H, OH, optionally (un)substituted aryl (substitution as defined by X below), (un)substituted heterocycle (substitution as defined by X below), $-(CH_2)_nOR^3$
R"=H, OH, OR'
X and X' independently=H, F, Cl, Br, I, OR', CN, OH, $S(O)_{n2}R^4$, $CF_3$, $R^4$, $NO_2$
$R^4=C_{1-6}$ (un)branched alkyl
$m=0-3$
$m'=0-5$
W=O,H Preferred compounds for use in the pharmaceutical compositions or method of the present invention are those of Formula I wherein:
R=H, $C_{1-2}$ alkyl
Y=NR'R"
R'=H, $C_{1-6}$ (un)branched alkyl, $-(CH_2)_nZ(CH_2)_n\cdot A$
Z=nothing, O, $CHOR^3$, $NR^3$
$R_3=$H
A=H, OH, (un)substituted aryl (substitution as defined by X below)
X and X' independently=H, F, Cl, Br, CN, $CF_3$, OR', $SR^4$, $R^4$
R"=H
$R^4=C_{1-4}$ (un)branched alkyl
$m=0-2$
$m'=0-2$
W=H
$n=2-4$
$n'=0-3$ The most preferred compounds for use in the compositions or method of the present invention are 2-Amino-3-(4-fluorobenzoyl)-phenylacetamide; 2-Amino-3-benzoyl-phenylacetamide; and 2-Amino-3-(4-chlorobenzoyl)-phenylacetamide.

The preparation of the compounds of Formula I, Formula VII and Formula IX may be accomplished by the reactions outlined in the following scheme:

[Reaction scheme shown: Compound II (substituted 2-aminobenzophenone with (X)_m' and (X)_m) + RCH(SR^4)COY → III]

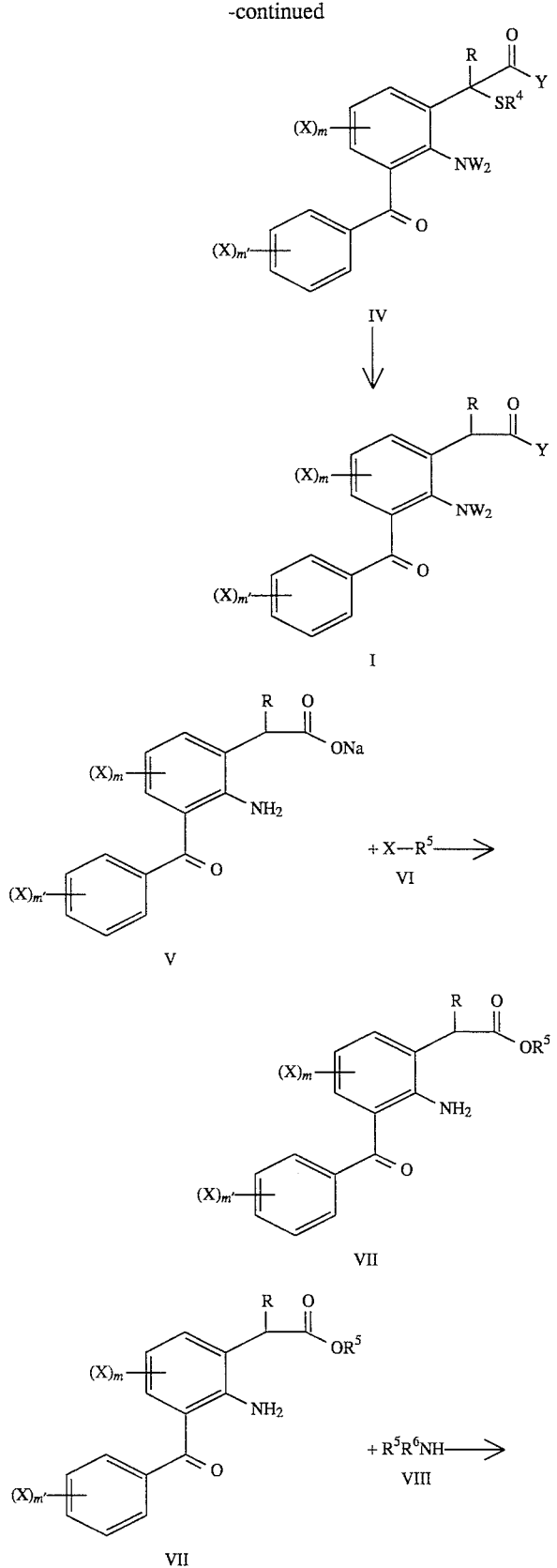

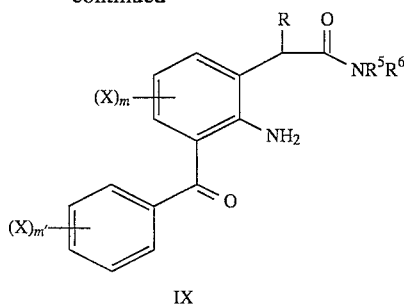

IX wherein X, Y, R, $R^4$, $R^5$, $R^6$, m, m', and W are as defined above. The general method for the preparation for compounds of Formula I and Formula IV where Y is such that the compound is an amide derivative and W is hydrogen are detailed in U.S. Pat. No. 4,313,949 assigned to A. H. Robins. The general method for preparing compounds of Formula V and detailing the conversion of compounds of Formula V into compounds of the Formula VII are described in U.S. Pat. Nos. 4,045,576, 4,503,073, 4,182,774, and 4,126,635 all assigned to A. H. Robins, and by the methods of Walsh et al., (J. Medicinal Chemistry, volume 27, 1984, pages 1379–88 and J. Medicinal Chemistry, volume 33, 100, pages 2296–2304). Compounds of Formula VI where X' is a suitable leaving group such as Cl, Br, I, or organic sulfonate (mesylate, tosylate) and $R^5$ is as described above, may be prepared by one skilled in the art. Amides of Formula IX may be formed by reacting esters of Formula VII (preferably ethyl or methyl esters) with the appropriate amine of Formula VIII either neat or in the presence of a solvent such as dimethyl formamide, dimethyl sulfoxide or acetonitrile at temperatures between 0° and 150° C. Amines of Formula VIII, may be prepared by one skilled in the art.

The synthesis of compounds of Formula I and the carboxylic acid of Formula X where W is oxygen is detailed in U.S. Pat. No. 4,254,146 assigned to A. H. Robins and is outlined below. The required amine or alcohol (Formula XI) is commercially available or can be readily prepared by one skilled in the art.

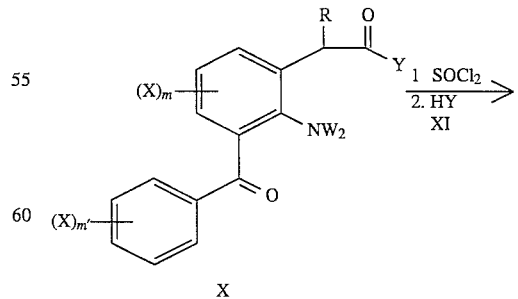

X

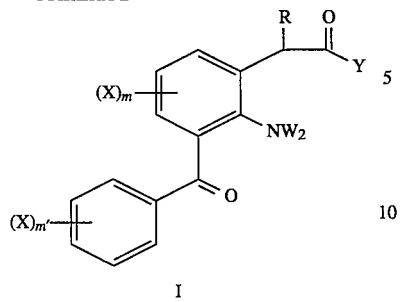

I

The manipulation of suitable protecting groups and deprotecting steps as employed by one skilled in the art may be necessary for the preparation of compounds of Formula I, Formula IV, Formula VIII, Formula IX and required intermediates.

The invention will be further illustrated by the following examples which are intended to be illustrative, but not limiting.

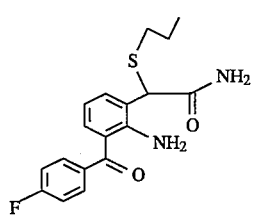

Compound 1
2-Amino-3-(4-fluorobenzoyl)-α-(n-propylthio)-phenylacetamide

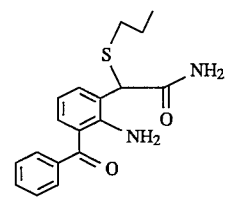

Compound 2
2-Amino-3-benzoyl-α-(n-propylthio)-phenylacetamide

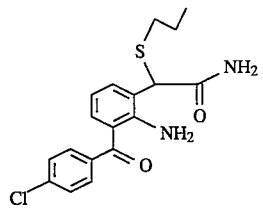

Compound 3
2-Amino-3-(4-chlorobenzoyl)-α-(n-propylthio)-phenylacetamide

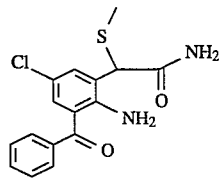

Compound 4
2-Amino-3-benzoyl-5-chloro-α-(methylthio)-phenylacetamide

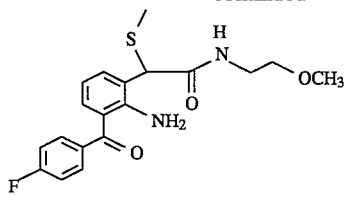

Compound 5
2-Amino-3-(4-fluorobenzoyl)-α-(methylthio)-N-(2-methoxy)ethyl acetamide

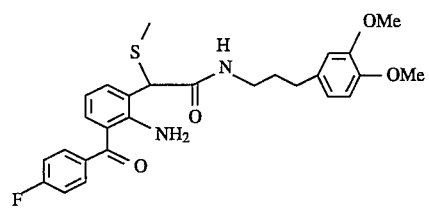

Compound 6
2-Amino-3-(4-fluorobenzoyl)-α-(methylthio)-N-3-(3,4-dimethoxyphenyl)propyl phenylacetamide

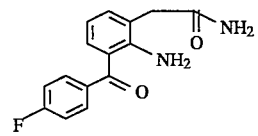

Compound 7
2-Amino-3-(4-fluorobenzoyl)-phenylacetamide

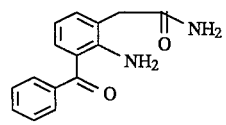

Compound 8
2-Amino-3-benzoyl-phenylacetamide

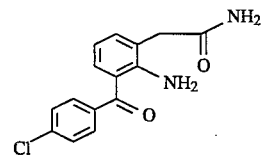

Compound 9
2-Amino-3-(4-chlorobenzoyl)-phenylacetamide

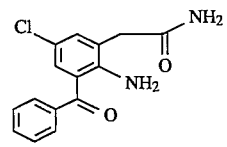

Compound 10
2-Amino-3-benzoyl-5-chlorophenylacetamide

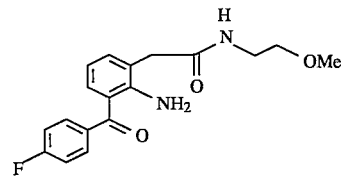

Compound 11
2-Amino-3-(4-fluorobenzoyl)-N-(2-methoxy)ethyl phenylacetamide

-continued

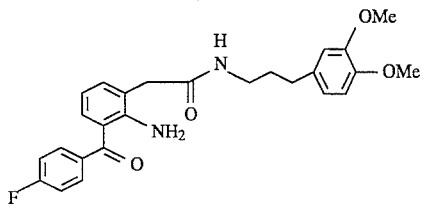

Compound 12
2-Amino-3-(4-fluorobenzoyl)-N-3-(3,4-dimethoxyphenyl) propyl phenylacetamide

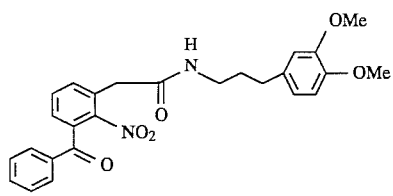

Compound 13
3-Benzoyl-2-nitrophenyl-N-3-(3,4-dimethoxyphenyl) propyl acetamide

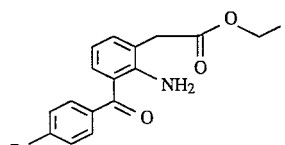

Compound 14
Ethyl 2-amino-3-(4-bromobenzoyl)-benzene acetate

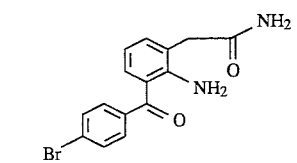

Compound 15
2-Amino-3-(4-bromobenzoyl)-phenylacetamide

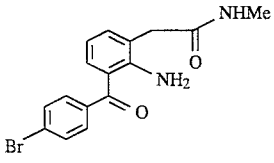

Compound 16
2-Amino-3-(4-bromobenzoyl)-N-methyl-phenylacetamide

PREPARATION I

2-Amino-3-(4-fluorobenzoyl)-α-(n-propylthio)-phenylacetamide, Compound 1

A solution of 21.5 g (0.1 mole) of 4'-fluoro-2-aminobenzophenone in 400 mL of methylene chloride was cooled to −70° C. and 11.5 g (0.1 mole) of 95% t-butylhypochlorite was added over a period of 15 min, keeping the temperature below −66° C. To this solution was added a solution of 13.3 g of 2-n-propylthioacetamide in 50 mL of methylene chloride over a 10 min period. The solution was stirred for 1 h at −65° to −70° C. and then allowed to warm to 0° C. at which point 10.2 g (0.1 mole) of triethylamine was added. The solution was stirred for 10 min and then washed with water. The organic solution was dried over magnesium sulfate. After concentrating under reduced pressure, the residue was crystallized from isopropyl alcohol and dried to give 19.5 g (56%) of yellow crystals melting at 140°–142° C.

Analysis: Calculated for $C_{18}H_{19}N_2O_2SF$: C, 62.41; H, 5.53; N, 8.09. Found: C, 62.34; H, 5.58; N, 8.04.

PREPARATION II

2-Amino-3-benzoyl-α-(n-propylthio)-phenylacetamide, Compound 2

In the same manner as given in Preparation 1,2-amino-3-benzoyl-α-(n-propylthiophenylacetamide, Compound 2, is prepared from 2-aminobenzophenone, t-butylhypochlorite and 2-n-propylthioacetamide.

PREPARATION III

2-Amino-3-(4-chlorobenzoyl)-α-(n-propylthio)-phenylacetamide, Compound 3

In the same manner as given in Preparation 1,2-amino-3-(4-chlorobenzoyl)-α-(n-propylthio)-phenylacetamide, Compound 3, is prepared from 4'-chloro-2-aminobenzophenone t-butylhypochlorite and 2-n-propylthioacetamide.

PREPARATION IV

2-Amino-3-benzoyl-5-chloro-α-(methylthio)-phenylacetamide, Compound 4

To a cold (−70° C.) solution of 12.77 g (0.055 mole) of 2-amino-5-chlorobenzophenone in 300 mL of methylene chloride, under nitrogen atmosphere, was added 6.0 g (0.552 mole) of t-butylhypochlorite in 20 mL of methylene chloride. After the reaction was stirred for an additional 15 min, a suspension of 5.8 g (0.055 mole) of α-(methylthio)acetamide in 150 mL of methylene chloride was added. The mixture was stirred at −65° C. for 1 h. Triethylamine (5.6 g, 0.055 mole) was added and the solution was allowed to warm to room temperature. The reaction mixture was extracted with water and the organic layer dried over magnesium sulfate. The volume of the solution was reduced in vacuo to about 200 mL and the product crystallized as a yellow solid, m.p. 173.5°–174.5° C. Yield was 6.86 g (37.3%).

Analysis: Calculated for $C_{16}H_{15}N_2O_2SCl$: C, 57.40; H, 4.52; N, 8.36. Found C, 57.38; H, 4.50; n, 8.51

PREPARATION V

2-Amino-3-(4-fluorobenzoyl)-α(methylthio)-N-(2-methoxy)ethylacetamide, Compound 5

To a solution of 21.5 g (0.1 mole) of 2-amino-4'-fluorobenzophenone in 400 mL of methylene chloride cooled to −70° C. is added 11.5 g (0.1 mole) of 95% t-butylhypochlorite over 15 min, keeping the temperature below −66° C. To this solution is added a solution of α-(methylthio)-N-(2-methoxyethyl)acetamide (0.1 mole) in 50 mL of methylene chloride over a ten minute period. The solution is stirred for 1 h at −65° to −70° C. and then is allowed to warm to 0° C. Triethylamine (0.1 mole) is added and the resulting solution is washed with water. The organic solution is dried with magnesium sulfate, and concentrated in vacuo. The product is isolated using standard conditions.

PREPARATION VI

2-Amino-3-(4-fluorobenzoyl)-α(methylthio)-N-3-(3,4-dimethoxyphenyl)propyl acetamide, Compound 6

To a solution of 21.5 g (0.1 mole) of 2-amino- 4'-fluorobenzophenone in 400 mL of methylene chloride, cooled to −70° C. is added 11.5 g (0.1 mole) of 95% t-butylhypochlorite over 15 min, keeping the temperature below −66° C. To this solution is added a solution of α-(methylthio)-N-3-(3, 4-dimethoxyphenyl)propylacetamide (0.1 mole) in 50 mL of methylene chloride over a ten minute period. The solution is stirred for 1 h at −65° to −70° C. and then is allowed to warm to 0° C. Triethylamine (0.1 mole) is added and the resulting solution is washed with water. The organic solution is dried with magnesium sulfate, and concentrated in vacuo. The product is isolated using standard conditions.

PREPARATION VII

2-Amino-3-(4-fluorobenzoyl)-phenylacetamide, Compound 7

A solution of 24.2 g (0.07mole) of 2-amino-3-(4-fluorobenzoyl)-α-(n-propylthio)phenylacetamide in 300 mL of tetrahydrofuran was treated with an excess of wet Raney nickel (washed three times with water and three times with tetrahydrofuran). The mixture was stirred for 1 h and filtered. The filtrate was concentrated under reduced pressure and the residue was crystallized from 95% ethanol to afford 14.8 g (78%) of yellow needles melting at 184°–186° C.

Analysis: Calculated for $C_{15}H_{13}N_2O_2F$: C, 66.17; H, 4.81; N, 10.29. Found: C, 66.32; H, 4.81;N, 10.48.

PREPARATION VIII

2-Amino-3-benzoyl-phenylacetamide, Compound 8

In the same manner as given in Preparation VII, 2-amino-3-benzoylphenylacetamide is prepared from 2-amino-3-benzoyl-α-(n-propylthio)phenylacetamide.

PREPARATION IX

2-Amino-3-(4-chlorobenzoyl)-phenylacetamide, Compound 9

In the same manner as given in Preparation VII, 2-amino-3-(4-chlorobenzoyl)phenylacetamide is prepared from 2-amino-3-(4-chlorobenzoyl)-α-(n-propylthio)phenylacetamide.

PREPARATION X

2-Amino-3-benzoyl-5-chlorophenylacetamide, Compound 10

A mixture of 21.34 g (0.0639 mole) of 2-amino-benzoyl-5-chloro-α-(methylthio)phenylacetamide and excess Raney nickel in a mixture of 900 mL absolute ethanol, and 200 mL dimethylformamide was stirred at room temperature for 45 min. The mixture was filtered through celite to remove Raney nickel. The solvent was removed under reduced pressure to give a yellow solid which was recrystallized to give a solid, m.p. 213.5°–215.0° C. (d).

Analysis: Calculated for $C_{15}H_{13}N_2O_3Cl$: C, 62.40; H, 4.54; N, 9.70. Found: C, 62.35; H, 4.58; N, 9.74.

PREPARATION XI

2-Amino-3-(4-fluorobenzoyl)-N-(2-methoxy)ethyl phenylacetamide, Compound 11

A mixture of 0.07 mole of 2-amino-3-(4-fluorobenzoyl)-α-(methylthio)-N-(2-methoxy)ethylacetamide in 300 mL of tetrahydrofuran is treated with an excess of wet Raney nickel (washed three times with water and three times with tetrahydrofuran). The mixture is stirred for 1 h and filtered. The filtrate is concentrated under reduced pressure and the residue is purified by standard procedures to give the product.

PREPARATION XII

2-Amino-3-(4-fluorobenzoyl)-N-3-(3,4-dimethoxyphenyl)propyl phenylacetamide, Compound 12

A mixture of 0.07 mole 2-amino-3-(4-fluorobenzoyl)-α-(methylthio)-N-3-(3,4-dimethoxyphenyl) propylacetamide in 300 mL of tetrahydrofuran is treated with an excess of wet Raney nickel (washed three times with water and three times with tetrahydrofuran). The mixture is stirred for 1 h and filtered. The filtrate is concentrated under reduced pressure and the residue is purified by standard procedures to give the product.

PREPARATION XIII

3-Benzoyl-2-nitrophenyl-N-3-(3,4-dimethoxyphenyl)propyl acetamide, Compound 13

A mixture of 0.028 mole of 3-benzoyl-2-nitrobenzeneacetic acid, 50 mL of thionyl chloride and 50 mL of benzene is heated at reflux. The dark solution is concentrated under vacuum. The residue is diluted with benzene and concentrated under vacuum (twice). A portion of the acid chloride (0.01 3 mole) in tetrahydrofuran is added to a solution of 3-amino (3,4-dimethoxyphenyl)propane (0.015 mole). The mixture is stirred at room temperature and then added to 200 mL of cold water. The resulting mixture is extracted with diethyl ether. The combined extracts are washed with water, dried over sodium sulfate and concentrated under reduced pressure. The residue is purified using standard procedures to give the product.

PREPARATION XIV

Ethyl-2-Amino-3-(4-bromobenzoyl)benzene acetate, Compound 14

A slurry of 35.6 g (0.1 mole) of 2-amino-3-(bromobenzoyl)benzeneacetic acid in 500 mL of dimethylformamide was treated with 32.0 g (0.2 mole) of ethyl iodide and stirred at ambient temperature for 24 h. The mixture was filtered and the filtrate was poured into 3.5 l of water. The solid which precipitated was collected by filtration, washed with water and recrystallized from absolute ethanol to give 26.8 g (74%) of the title compound, as gold needles, m.p. 107°–109° C.

Analysis: Calculated for $C_{17}H_{16}BrNO_3$: C, 56.37; H, 4.45; N, 3.87. Found: C, 56.22; H 4.42; N, 3.87.

PREPARATION XV

2-Amino-3-(4-bromobenzoyl)-phenylacetamide, Compound 15

Ammonia is condensed in a tube containing 2-amino-3-(4-bromobenzoyl)benzeneacetic acid, ethyl ester. The tube is sealed and the reaction mixture is warmed. The sealed tube was cooled and opened. Solvent was evaporated and the residue was purified by standard methods to give Compound 15.

PREPARATION XVI

2-Amino-3-(4-bromobenzoyl)-N-methyl phenylacetamide, Compound 16

In the same manner as Preparation XV, 2-amino-3-(4-bromobenzoyl)-N-methyl phenylacetamide, Compound 16 is prepared from 2-amino-3-(4-bromobenzoyl)benzeneacetic acid, ethyl ester and methylamine.

Anti-Inflammatory Tests

I. In vitro Anti-Inflammatory Test

In vitro anti-inflammatory activity of 2-amino-3-benzoylbenzeneacetic acid analogues was tested by polarographically monitoring the inhibition in the rate of oxygen consumption (Cook H. W., Ford G., and Lands WEM, Anal. Biochem. 96:341, 1979) in the conversion of arachidonic acid to prostaglandin $H_2$ by prostaglandin H synthase (cyclooxygenase). Cyclooxygenase enzyme was prepared by solubilizing 20 mg of lipid-depleted sheep vesicular gland microsomal powder (Graff G., Stephenson J. H., et al., J. Biol. Chem. 253:7662, 1978) in 1.0 mL of buffer containing 50 mM phosphate, 5 mM diethyldithiocarbamic acid, and 2 µM hematin (pH 7.4). Incubations were carried out at 30° C. with a YSI-oxygen monitor (Model 53) in 50 mM phosphate/0.5 mM phenol buffer (pH 7.4) as described elsewhere (Graff G., and Anderson L. A., Prostaglandins 38:473, 1989).

II. Ex Vivo Anti-Inflammatory Test

Ex vivo anti-inflammatory activity of 2-amino-3-benzoylbenzeneacetic acid analogues was evaluated in naive New Zealand Albino (NZA) rabbits. In this test animals were dosed bilaterally with a single 50 µL aliquot of a 0.1% solution/suspension of vehicle, formulated test or reference compound. After 60 minutes of treatment, animals were euthanized, iris/ciliary body (ICB) quickly excised and placed into ice-cold PBS buffer (pH 7.4). The tissue was then weighed, homogenized in ice-cold 50 mM phosphate/ 0.5 mM phenol buffer (pH 7.4) and incubated for 10 minutes at 37° C. with 10 µM of $[1-^{14}C]$-20:4. Upon termination of the incubations, reaction products (prostaglandins) were isolated by organic solvent extraction (Bligh, E. G. and Dyer, W. J., Can. J. Biochem. Physiol. 37:911, 1959) and quantified by $C_{18}$-HPLC (Powell, W. S., Anal. Biochem.148:59 1985).

III. In Vivo Anti-Inflammatory Test

In vivo anti-inflammatory activity of 2-amino-3-benzoylbenzeneacetic acid analogues was evaluated in the model of trauma-induced breakdown of the blood-aqueous-barrier in New Zealand Albino (NZA) rabbits. Animals were anesthetized prior to bilateral administration of a single topical 50 µL dose of a 0.1% solution/suspension of formulated test or reference compound. After 45 minutes of treatment ocular trauma was induced by paracentesis. Thirty minutes postparacentesis animals were euthanized, and aqueous humor was removed for protein (Bradford, M. M., Anal. Biochem. 72:248, 1976) and $PGE_2$ analysis (Radio immune assay, NEN-Research Products, E. I. Du Pont de Nemours, Boston, Mass.).

Results

The results from in vitro, ex vivo and in vivo anti-inflammatory tests are summarized in Table 1. Non-halogenated and halogenated 2-amino-3-benzoylbenzeneacetic acid analogues with free carboxylic acid functional groups, including the reference compound diclofenac, were potent in vitro inhibitors of sheep vesicular gland cyclooxygenase activity with $IC_{50}$ values ranging from 0.029 to 0.250 µM. When tested in vivo, they effectively inhibited trauma-induced accumulation of $PGE_2$ ($\geq 98\%$) and plasma protein influx into the aqueous humor in vivo. Similar results were obtained with the reference compound, diclofenac, which was somewhat less effective both in vitro and in vivo than the chloro- or bromo- substituted 2-amino-3-benzoylbenzeneacetic acids.

In contrast, unsubstituted and mono-substituted amide analogues of 2-amino- 3-benzoylbenzeneacetic acid (Compounds 7, 8, 9, 15 and 16) were $\geq 3$ orders of magnitude less effective inhibitors of cyclooxygenase activity in vitro with $IC_{50}$ values ranging from 16 to >133 µM. Despite their weak inhibitory effects on cyclooxygenase activity in vitro, they were as effective as, or in one instance (Compound 7) more effective than, free carboxylic acid analogues in inhibiting plasma protein influx into the anterior chamber (62 to 72%) and aqueous humor $PGE_2$ accumulation (>93%). Interestingly, the dimethyl substituted amide analog was inactive in both in vitro and in vivo tests.

Although the in vitro potency was clearly enhanced by halogenation of the 4-position of the benzoyl ring of 2-amino-3-benzoylbenzeneacetic acid, there was little evidence for such a structure related effect in vivo.

When tested for ex vivo anti-inflammatory activity, Compound 8 was the most effective inhibitor of iris/ciliary body prostaglandin synthesis. The synthesis of all prostaglandins produced by the iris/ciliary body was inhibited to a similar extent. This spectrum of inhibition is in contrast to the effects of 2-amino-3-benzoylbenzeneacetic acid analogs with free carboxylic acid functional groups which predominately inhibited $PGE_2$ production.

Conversion of the free carboxylic acid functional group of Bromfenac to an ethyl ester (Compound 14) also resulted in a >3 orders of magnitude decline in in vitro cyclooxygenase inhibitory activity. However, when tested for topical ocular anti-inflammatory activity the ethyl ester showed significant inhibitory activity by reducing plasma protein extravasation into the aqueous humor by 60%.

TABLE 1

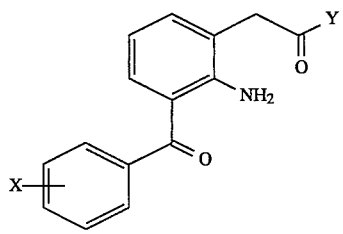

SUMMARY OF ANTI-INFLAMMATORY TEST RESULTS

| Compound | Substituent X | Y | In Vitro Cyclooxygenase Inhibition IC50 (uM) | Ex Vivo Iris/Ciliary Body Total Prostaglandin Synthesis Inhibition (%)*** | In Vivo Aqueous Humor PGE2 Accumulation Inhibition | In Vivo Paracentesis Protein Extravasation Inhibition (%)* |
|---|---|---|---|---|---|---|
| Diclofenac** | — | — | 0.120 | 50 | 97 | 54 |
| Amfenac | 4'-H | OH | 0.25 | — | — | 41 |
| — | 4'-F | OH | 0.171 | — | — | 42 |
| — | 4'-Cl | OH | 0.070 | — | 99 | 72 |
| Bromfenac | 4'-Br | OH | 0.029 | 44 | 98 | 62 |
| #15 | 4'-Br | NH2 | 19 | — | 97 | 64 |
| #16 | 4'-Br | NHCH3 | 16 | 48 | 93 | 62 |
| — | 4'-Br | N(CH3)2 | >>100 | — | −27 | 2 |
| #8 | H | NH2 | 64 | 81 | 98 | 61 |
| #7 | 4'-F | NH2 | 133 | 27 | 98 | 72 |
| #9 | 4'-Cl | NH2 | >>100 | 29 | 98 | 65 |
| #15 | 4'-Br | NH2 | 19 | 23 | 97 | 64 |
| #14 | 4'-Br | OCH2CH3 | >>25 | 33 | — | 60 |

*Single topical dose of a 0.1% drug solution/suspension 45 minutes prior to paracentesis
**Diclofenac, also known as Voltaren Opthalmic (TM), is used as a reference standard
***Single topical dose of 0.1% drug solution/suspension 60 minutes prior to iris/ciliary body isolation The 3-benzoylphenylacetic acid derivative compounds of this invention are useful for controlling ophthalmic inflammatory disorders and ocular pain. Such disorders include, but are not limited to uveitis, scleritis, episcleritis, keratitis, surgically-induced inflammation and endophthalmitis.

The 3-benzoylphenylacetic acid derivatives may be formulated into a variety of topically administrable ophthalmic compositions, such as solutions, suspensions, gels or ointment.

Pharmaceutical compositions comprising compounds of Formula 1 in aqueous solution, optionally containing a preservative for multidose use and other conventionally employed ophthalmic adjuvants, including a salt entity to adjust the tonicity of solutions, can be employed. The most preferred form of delivery is by eye drops; however, formulations wherein the final specialty form is a gel or ointment can also be employed and formulated according to conventional technology. The ophthalmic compositions of the present invention will typically contain one or more compounds of Formula 1 in an amount of from about 0.001 to about 4.0% (w/v), preferably from about 0.01 to about 0.5% (w/v).

Further, additional therapeutic agents including steroids, such as, dexamethasone; antibiotics, such as gentamicin; anti-infectives, such as sulfonamides; and antioallergics, such as antihistamines, may be added to supplement the ophthalmic compositions of the present invention.

The compositions may contain preservatives such as thimerosal, chlorobutanol, benzalkonium chloride, Onamer M, or chlorhexidine; buffering agents, such as phosphates, borates, carbonates and citrates; and thickening agents, such as, high molecular weight carboxy vinyl polymers, such as, the ones sold under the name of Carbopol which is a trademark of the B. F. Goodrich Chemical Company, hydroxyethylcellulose, or polyvinyl alcohol, for example.

The compositions are prepared by dissolving the various ingredients in the required amount of water with stirring to ensure that all the ingredients are dissolved. The aqueous compositions of the invention may be solutions, suspensions, or gels. After preparation of the solution, suspension, or gel the compositions are then packaged in dispensers suitable for delivery of the ophthalmic compositions.

The following examples of ophthalmic compositions typify the manner in which the invention may be practiced. The examples should be construed as illustrative, and not as a limitation upon the overall scope of the invention. The percentages are expressed on a weight/volume basis. "Active Agent" means one or more compounds of Formula I.

| | |
|---|---|
| Active agent | 0.01–0.5% |
| Polysorbate 80 | 0.01% |
| Benzalkonium Chloride | 0.01% + 10% excess |
| Disodium EDTA | 0.1% |
| Monobasic Sodium Phosphate | 0.03% |
| Dibasic Sodium Phosphate | 0.1% |
| Sodium Chloride | q.s. 290–300 mOsm/Kg |
| pH adjustment with NaOH and/or HCl | pH 4.2–7.4 |
| Water | q.s. 100% |

| | |
|---|---|
| Active Agent | 0.01–0.5% |
| Hydroxypropyl Methylcellulose | 0.5% |

| | |
|---|---|
| -continued | |
| Polysorbate 80 | 0.01% |
| Benzalkonium Chloride | 0.01% + 5% excess |
| Disodium EDTA | 0.01% |
| Dibasic Sodium Phosphate | 0.2% |
| Sodium Chloride | q.s. 290–300 mOsm/Kg |
| pH adjustment with NaOH and/or HCl | pH 4.2–7.4 |
| Water | q.s. 100% |

We claim:

1. A method of treating ophthalmic inflammatory disorders and ocular pain which comprises topically administering to the eye a pharmaceutical composition comprising an anti-inflammatory-effective amount of a 3-benzoylphenylacetic acid derivative of the formula:

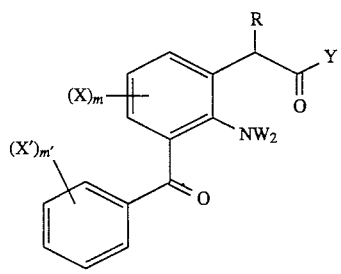

R=H, $C_{1-4}$ (un)branched alkyl, $CF_3$, or $SR^4$,
Y=NR"R',
R'=H, or $C_{1-10}$ (un)branched alkyl, (un)substituted (substitution as defined by X below),
R"=H,
X and X' independently=H, F, Cl, Br, I, OR', OH, $SR^4$, $CF_3$, $R^4$, or $NO_2$,
$R^4$=$C_{1-6}$ (un)branched alkyl,
m=0–3,
m'=0–5, and
W=H.

2. The method of claim 1 wherein the 3-benzoylphenylacetic acid derivative is of the formula:

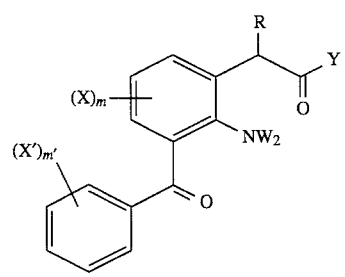

R=H, or $C_{1-2}$ alkyl
Y=NR'R",
R'=H, or $C_{1-6}$ (un)branched alkyl,
X and X' independently=H, F, Cl, Br, $CF_3$, OR', $SR^4$, or $R^4$,
R"=H,
$R^4$=$C_{1-4}$ (un)branched alkyl,
m=0–2,
m'=0–2, and
W=H.

3. The method of claim 1 wherein the 3-benzoylphenylacetic acid derivative is selected from the group consisting of 2-Amino-3-(4-fluorobenzoyl)-α-(n-propylthio)-phenylacetamide, 2-Amino-3-benzoly-α-(n-propylthio)-phenylacetamide, 2-Amino-3-(4-chlorobenzoyl)-α-(n-propylthio)-phenylacetamide, 2-Amino-3-benzoyl-5-chloro-α-(methylthio)-phenylacetamide, 2-Amino-3-(4-fluorobenzoyl)-α-(methylthio)-N-(2-methozy)ethylacetamide, 2-Amino-3-(4-fluorobenzoyl)-phenylacetamide, 2-Amino-3-benzoyl-phenylacetamide, 2-Amino-3-(4-chlorobenzoyl)-phenylacetamide, 2-Amino-3-benzoyl-5-chlorophenylacetamide, 2-Amino-3-(4-fluorobenzoyl)-N-(2-methoxy)ethyl phenylacetamide, 2-Amino-3-(4-bromobenzoyl)-phenylacetamide, and 2-Amino-3-(4-bromobenzoyl)-N-methyl phenylacetamide.

4. The method claim 3 wherein the 3-benzoylphenylacetic acid derivative is selected from the group consisting of 2-Amino-3-(4-fluorobenzoyl)-α-(n-propylthio)-phenylacetamide, 2-Amino-3-(4-chlorobenzoyl)-α-(n-propylthio)-phenylacetamide, 2-Amino-3-(4-chlorobenzoyl)-α-(n-propylthio)-phenylacetamide, 2-Amino-3-benzoyl-5-chloro-α-(methylthio)-phenylacetamide, 2-Amino-3-(4-fluorobenzoyl)-phenylacetamide, 2-Amino- 3-benzoyl-phenylacetamide, 2-Amino-3-(4-chlorobenzoyl)-phenylacetamide, 2-Amino-3-benzoyl-5-chlorophenylacetamide, and 2-Amino-3-(4-bromobenzoyl)-phenylacetamide.

5. The method of claim 4 wherein the 3-benzoylphenylacetic acid derivative is selected from the group consisting of 2-Amino-3-(4-fluorobenzoyl)-phenylacetamide, 2-Amino-3-benzoyl-phenylacetamide and 2-Amino-3-(4-chlorobenzoyl)-phenylacetamide.

6. The method of claim 1 wherein the amount of 3-benzoylphenylacetic acid is from about 0.001 to about 4.0% (w/v).

7. The method of claim 6 wherein the amount of 3-benzoylphenylacetic acid is from about 0.01 to about 0.5% (w/v).

* * * * *